United States Patent [19]

Urist

[11] 4,455,256

[45] * Jun. 19, 1984

[54] BONE MORPHOGENETIC PROTEIN

[75] Inventor: Marshall R. Urist, Pacific Palisades, Calif.

[73] Assignee: The Regents of the University of California, Berkley, Calif.

[*] Notice: The portion of the term of this patent subsequent to Oct. 13, 1998 has been disclaimed.

[21] Appl. No.: 260,726

[22] Filed: May 5, 1981

[51] Int. Cl.³ .............................................. C07G 7/00
[52] U.S. Cl. .............................. 260/112 R; 260/118; 260/123.7; 424/95; 424/177
[58] Field of Search ........................... 260/112 R, 118

[56] References Cited

U.S. PATENT DOCUMENTS

| | | | |
|---|---|---|---|
| 2,384,673 | 9/1945 | Greffie | 260/118 |
| 2,717,835 | 9/1955 | Brody | 260/112 R |
| 3,539,549 | 11/1970 | Greenfield | 260/112 R |
| 3,887,717 | 6/1975 | Pfeiffer et al. | 260/112 P |
| 4,294,753 | 10/1981 | Urist | 260/112 R |

OTHER PUBLICATIONS

Lancet, May 2, 1981, pp. 959-962, Glowacki et al.
Proc. Nat. Acad. Sci USA, (1979), 76(4), pp. 1828-1832, Urist et al.
Urist, Science, 150, pp. 893-899, (1965).
Proc. Soc. Exptl. Biology & Med., 162:48-53, (1979), Urist et al.
Urist et al., 15 (4), 269-286, (1974), Calcified Tissue Research.
Urist et al., Clin. Orthop. Rel. Res. 53,243-283, (1967).
Urist et al., Proc. Soc. Exp. Bio. and Med. 162, 48-53, (1979).
Urist et al., Proc. Natl. Acad. Sci. USA 76 (4), 1828-1832, Apr. 1979.

Primary Examiner—Howard E. Schain
Attorney, Agent, or Firm—Kenyon & Kenyon

[57] ABSTRACT

Bone morphogenetic protein (BMP) made by the process comprising the steps of demineralizing bone tissue; treating the demineralized bone tissue under aqueous conditions with a water soluble neutral salt and a solubilizing agent for the BMP, the agent being selected from the group consisting of urea and guanidine, and thereby transforming the bone collagen to gelatin and extracting BMP into the solution of solubilizing agent; and separating the solubilizing agent and neutral salt from the solution, thereby precipitating BMP in the aqueous medium, and the BMP has a molecular weight in the range of 1,000-100,000.

20 Claims, 1 Drawing Figure

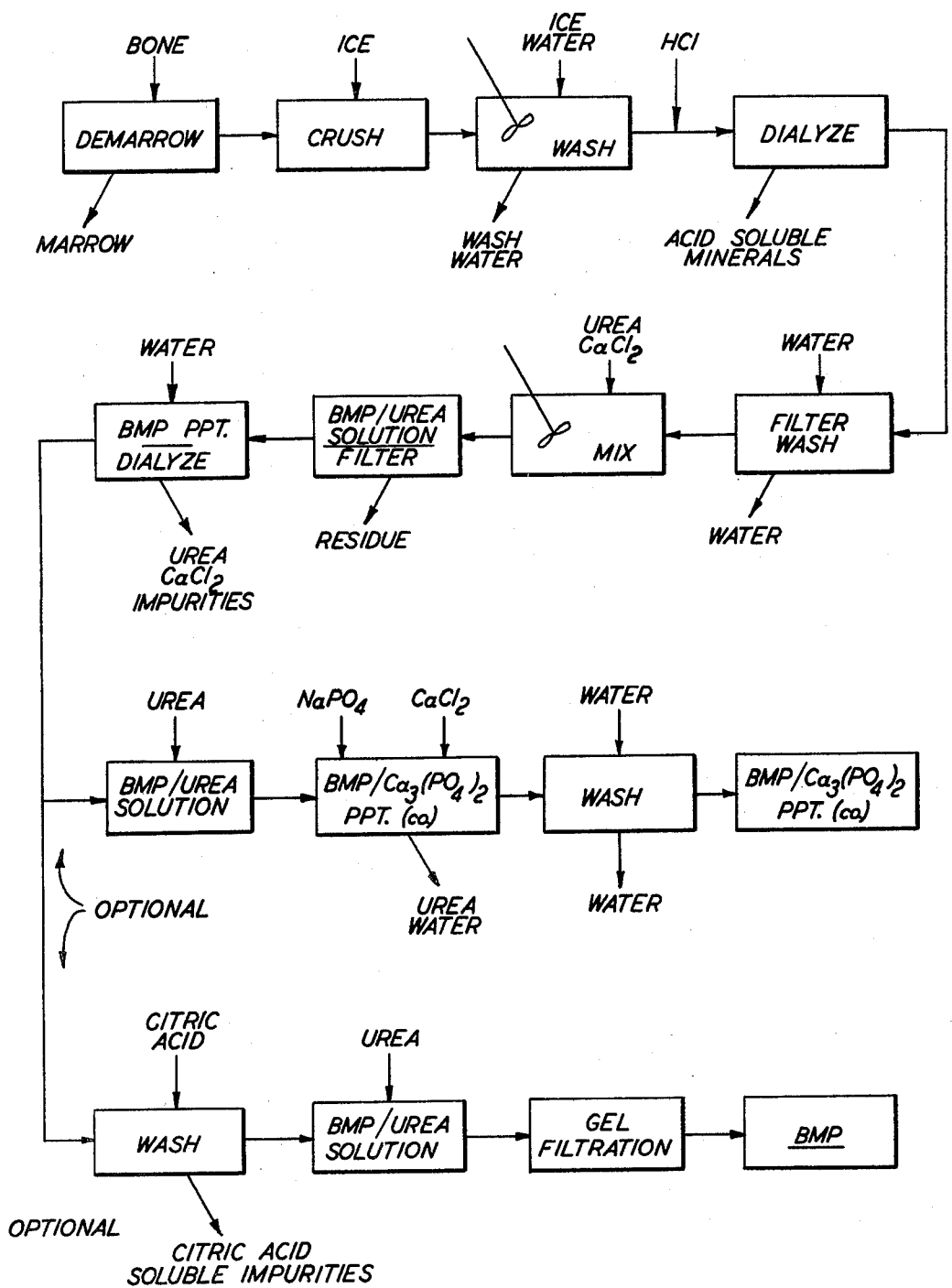

BONE MORPHOGENETIC PROTEIN

The invention described herein was made in the course of work under a grant or award from the Department of Health and Human Services.

This is a continuation application of my application Ser. No. 174,906 filed Aug. 4, 1980, now U.S. Pat. No. 4,294,753.

This invention relates to the preparation of chemical agents that cause bone tissue to form or grow. Such agents are separated from bone tissue. More particularly, the invention relates to a process for separation of bone inducing chemical agents, referred to as bone morphogenetic protein (BMP), from bone tissue under controlled conditions.

When cellular differentiation is attributed to the physicochemical effect of one tissue upon and in contact with another, the mechanism is known as induction. When a tissue transmits the bone induction protein, it produces differentiation of osteoblasts, and the process is called bone induction. Like an embryonic induction system, a bone induction system is composed of inducing cells and responding cells. An inducing cell is a cell that has had contact with the bone induction principle and induces a responding cell to differentiate into an osteoblast. The responding cell usually is a perivascular hypertrophied mesenchymal cell, and it becomes an induced cell when it differentiates into an osteoblast, a chondroblast, or a preosteoblast.

Once a bone induction system is established, one layer of induced cells may become the inducing cells for the next layer of responding cells. Induction occurs in two directions: centrifugally, to produce lamellar bone; centripetally, to remodel and become colonized by blood borne bone marrow precursor cells. The process continues until undifferentiated cells produce a large population of newly specialized cells arranged in the form of an organ. Thus, a bone induction system is a mechanism of organogenesis, that is, the development of an ossicle filled with bone marrow.

The applicant has previously discovered that demineralized bone matrix may be implanted into animals and new bone induced in soft tissue as a result. For example, reference is made to:

Urist, M. R.: Bone: Formation by Autoinduction, Science, 150:893-899, 1965;

Urist, M. R., Silverman, B. F., Buring, K., Dubuc, F. L. and Rosenberg, J. J.: The Bone Induction Principle, Clin. Orthop. Rel. Res., 53:243-283, 1967; and Urist, M. R., Earnest, F., Kimball, K. M., DiJulio, T. P. and Iwata, H.: Bone Morphogenesis In Implants Of Residues Of Radioisotope Labelled Bone Matrix. Calcified Tissue Research, 15(4): 269-286, 1974.

In nature BMP is firmly attached to collagen and bone matrix which is about 90% collagen. It has now been found that the active material BMP in bone may be readily separated from demineralized bone by converting the BMP containing collagen into gelatin and then forming a solution of BMP. The concentrated form of BMP improves the efficiency of the bone induction system.

The active BMP material is believed to be comprised of various amino acids and consists of an individual protein entity. The following characteristics suggest that the morphogenetic factor in bone matrix is a protein, part of a protein, or a derivative of a protein. It is heat labile, (greater than 70° C.); inactivated by deamination, denitrophenylation, acetylation, formaldehyde or remazol black but not by nitration or borohydride reduction (Urist, M. R., Strates, B. S.: Bone Morphogenetic Protein, J.Dent. Res. 5(Supl.6):1392-1406, 1971). It is degraded without solubilization of collagen in neutral buffers by limited digestion with the enzymes trypsin and chymotrypsin. BMP is also degraded during solubilization by the enzymes papain, ficin and pronase. BMP is resistant to collagenase. One method of isolating BMP is in a digestive solution of collagenase in which it is found amongst a group of collagenase resistant proteins. (Urist, M. R. et al, Proceedings Nat. Acad. of Sci., 70:3551, 1973). BMP is also partially resistant to acidic enzymes such as pepsin and cathepsin (Urist, M. R., Iwata, H.: Preservation and Biodegradation Of The Morphogenesis Property Of Bone Matrix, J. Theor. Biol. 38:155-168, 1973) not degraded by exogenous non-proteolytic enzymes, e.g., DNases, RNases, phosphatases, amylases, hyaluronidases and phospholipases (Urist, M. D., Dowell, T. A., Hay, P. H., Strates, B. S.: Inductive Substrates For Bone Formation, Clin. Orthop. 59:59-96, 1968; Urist and Iwata, 1973, supra.); degraded by endogenous enzymes under conditions favorable for the action of a tissue specified neutral proteinase or BMPase (Urist, M. R., Iwata, H., Boyd, S. D., Ceccotti, P. L.: Observations Implicating An Extracellular Enzymic Mechanism Of Control Of Bone Morphogenesis, J. Histochem. & Cytochem. 22:88-103, 1974).

BMP, although firmly bound can be released from the matrix of bone and from the cells of certain bone tumors such as osteosarcoma. Soluble non-collagenous proteins have been isolated (Herring, G. M.: The Chemical Structure Of Tendon, Cartilage, Dentin And Bone Matrix, Clin. Orthop. 60:261-300, 1968); Veis, A., Spector, A. R., Carmichael, D. A.: The Organization And Polymerization Of Bone And Dentin Collagens, Clin. Orthop. 66:188-211, 1969; Nusgens, B., Chantraine, A., Lapiere, C. M.: The Protein In Matrix Of Bone, Clin. Orthop., 88:252-273, 1972) by chemical extraction of bone matrix with cold ethylenediaminetetraacetic acid. These constituents, to a considerable extent, can be removed from bone matrix without a commensurate reduction in bone morphogenetic properties (Iwata, H., Urist, M. R.: Protein Polysaccaharide Of Bone Morphogenetic Matrix, Clin. Oethop., 87:257-274, 1972).

The process of this invention consists of isolation of BMP from two main sources*: (1) the organic matrix of bones and teeth of animals: (2) the cells of bone tumors. The BMP obtained from either source is classified as a glycoprotein. Many glycoproteins are found in animal bones and tumors, but not all glycoproteins have BMP activity. BMP activity is found in the proteins isolated by the process of isolation herein disclosed. When BMP is extracted from its place of storage in the matrix, it is recovered in the form of a relatively small molecule.

*Other processes have been previously described: See: Urist, M. R., Mikulski, A. J.: A Soluble Bone Morphogenetic Protein Extracted From Bone Matrix With A Mixed Aqueous And Nonaqueous Solvent (40616), Proc. Soc. Exp. Bio. and Med. 162:48-53, 1979; Urist, M. R., Mikulski, A., Lietze, A.: Solubilized And Insolubilized Bone Morphogenetic Protein, Proc. Natl. Acad. Sci. USA., 76(4): 1828-1832, April 1979.

Briefly, the present invention comprises low temperature demineralization of bone tissue followed by low temperature conversion of BMP-containing bone collagen to gelatin and solubilization of BMP therefrom. The BMP is then separated from the solution and used as an implant to fill bone defects.

The process of isolation of BMP involves the sequential steps of crushing and cleaning fresh demarrowed bone tissue at reduced temperatures. The crushed bone is then demineralized by dialysis from 0.6N HCl in dialysis bags whereby the acid soluble minerals in the bone tissue diffuse through the dialysis membrane into a surrounding acid solution. Thereafter, the BMP and other substances including bone solids remain in the dialysis bag. The supernatant HCl solution is filtered to remove cellular debris, cells and solid particles, and then washed free of HCl. A small fraction of the total tissue BMP can be recovered from the HCl solution in the sacs, but the larger fraction remains in the bone matrix for subsequent extraction.

The demineralized matrix, which is in the form of a rubbery mass, is then admixed with a cold aqueous solution of a neutral salt, such as calcium chloride, and a solubilizing agent for BMP. The salt converts the bone collagen to gelatin allowing ready separation of the BMP from the gelatin and solubilization of the BMP. Urea is particularly preferred as the solubilizing agent, although guanidine may also be used.

The liquid fraction (preferably the BMP-calcium chloride-urea aqueous solution) is dialyzed to remove the salt, the solubilizing agent, and other impurities. As the concentration of solubilizing agent decreases, the BMP precipitates in the cold water environment. Dialysis may be carried out against a dilute aqueous solution of ethylene glycol (about 0.01%) to stabilize the biologically active hydrophobic BMP molecule.

The nondialyzable precipitate substance, when analyzed biochemically, is found to comprise polypeptides and low molecular mass proteins, and has powerful BMP activity when bioassayed directly in muscle pouches, diffusion chambers and tissue culture.

The BMP containing precipitate may then be resolubilized in an aqueous solution of the solubilizing agent, i.e., urea, for further purification and concentration as hereinafter described. The aqueous solution containing BMP is reprecipitated as a coprecipitate admixture with a calcium salt such as calcium phosphate. Preferably, the calcium phosphate is formed from calcium chloride and sodium phosphate which are added sequentially to the aqueous solution. After further washing, the coprecipitate is ready for implanting. The active BMP material in the coprecipitate with calcium phosphate is used to advantage for implantation in bone defect caused by injury, malignancy, infection and congenital absence of bone.

Calcium carbonate and other insoluble calcium salts may be substituted for calcium phosphate. For example, calcium silicate or calcium oxalate or any other calcium salt can be used but they are not as well-tolerated and non-toxic as the preferred calcium phosphates.

Optionally, the dialyzed BMP precipitate may be washed with citric acid to remove acid soluble impurities, resolubilized with urea and fractionated in various gel filtration columns.

Bone matrix is approximately 90% collagen. Although urea (or guanidine) does extract a soluble BMP from collagen, it does so in very small quantities, namely, in the range of less than 1%. However, I have found that BMP is more readily removed from gelatin. Up to 100% of the available BMP has been removed from bone matrix whose collagen content has been transformed to gelatin and thereafter extracted by the calcium salt/solubilizing agent process herein disclosed. This has been determined by measuring substantially no BMP activity in the remaining bone matrix after the calcium chloride/urea extraction.

It has also been found that the greatest BMP activity is observed in the fraction whose molecular weight is in the range of 1,000–100,000, and preferably 10,000–50,000. Therefore, the dialysis membranes used in this process preferably have maximum pore sizes that permit diffusion of molecules in the range of up to about 10,000 molecular weight, and preferably between 3,500 and 10,000. Likewise, the gel filtration step, when used, involves seives in the molecular weight range of 1,000–100,000.

Since BMP has been found to be relatively insoluble in deionized cold water, it is preferred to carry out all BMP precipitation steps at cold water temperatures in the range of about 2°–5° C. Also, reduced temperatures reduces the chances for protein denaturization. With solutions of BMP in urea or guanidine, the temperature of the solution can be maintained at about room temperature.

In place of calcium chloride, any other water soluble physiologically acceptable neutral salt may be used to transform collagen into gelatin. For example, high concentration of lithium chloride, sodium chloride and potassium chloride or 0.5M strontium chloride, or other comparable salts may be used for the collagen conversion. However, calcium chloride is preferred since it is one of the most efficient and the most physiologic because it is well tolerated when bound to protein in the form of a calcium-protein complex; it is relatively non-toxic.

As stated above, guanidine may be used in place of, or in addition to urea as the solubilizing agent. The combination of the neutral salt and solubilizing agent may be referred to as the inorganic-organic solvent mix.

The preferred aqueous molar solutions are 0.5M for the preferred neutral salt, calcium chloride, and 6M urea and 4M guanidine.

In actual practice, freeze dried BMP or BMP/calcium phosphate coprecipitate is used as implanting material. It has been found that 1 mg of purified BMP, when packed into a bone defect of a rat or rabbit will cause the production of about 1 gram (wet weight) of bone. Grossly visible evidence of new bone first appears in about three weeks after implant and continues to remodel for about six months.

The molecular weight of BMP has been found to range between about 20,000 and about 63,000. Work with BMP material isolated from rabbit dentin matrix protein fraction, using polyacrylamide gel electrophoresis has been assigned a molecular weight of about 23,000. Since the 63,000 molecular weight preparation was prepared from osteosarcoma cells, while the 23,000 molecular weight preparation was obtained from cell free dentin matrix, it is possible that the matrix free proteins may be a proBMP and the matrix protein may be BMP. In any event, both the bone derived and osteosarcoma derived protein fractions have BMP activity when bioassayed either in diffusion chambers in rabbit or rat muscle pouches or in pellets in the mouse thigh.

The following specific examples are illustrative of the invention and will demonstrate the preparation of BMP and its method of use.

EXAMPLE 1

In a specific example of the process of this invention, as generally represented in the accompanying figure, 100 grams of rabbit (or bovine, rat or human) bone tissue freshly excised within hours from the vertebrate animal is demarrowed using a water pik, crushed with ice to avoid heating and washed in ice cold water. Washing is performed with agitation and repeated at least 3 times or until the bone is cleaned of blood and extraneous soft tissue.

The washed bone particles, preferably about 1 to 5 mm$^3$ in size, are mixed with ice cold 0.6N HCl and placed in cellulose acetate dialysis tubes. The molecular weight size range of the dialysis tubes is between 3,500 and 10,000. The volume ratio is 1 part bone particles to 10 parts 0.6N HCl, (although acid volumes up to about 100 parts of such acids as phosphoric and citric may also be used). The dialysis bags are immersed in large beakers containing ice cold 0.6N HCl for 24 hours or the minimal period of time necessary to demineralize the bone particles. Demineralization is considered complete when the solution phase is free of calcium ion. A silver nitrate test for chloride ion is taken as a measure of calcium ion remaining in the tube. Magnetic stirers are used in the beakers. The HCl in the beakers surrounding the bone-enclosed dialysis bags is changed 3 times or even more frequently within 24 hours, thus removing the acid soluble calcium phosphate, amino acids, peptides, and other dialyzable substances of low molecular mass.

After 24 hours, or when demineralization is complete, the dialysis bags are removed from the HCl bath. The matrix-supernatant HCl in the dialysis bags is washed three times in cold water containing 5 m.moles/l. of sodium azide and then filtered through cellulose acetate membranes having a pore size of about 0.22 microns to remove cellular debris, cells and small solid particles. The filtration process is carried out in a cold room at about 4° C. HCl solution is saved for future collection of minor proportions of BMP by dialysis against cold water.

The solid matrix material may be transferred to (clean) sterile beakers with sterile distilled water and suspensions of the precipitate may be preserved by freeze-drying (lyophilization).

The matrix material is then sequentially treated with 1:1 volume chloroform to methanol; 2M calcium chloride; 0.5M EDTA ethylene diamine tetraaacetic acid; and 6M lithium chloride; and water.

64 grams of the demineralized bone is added to 800 ml. of an aqueous solution of 6M urea and 0.5M calcium chloride. Collagen is thereupon transformed to gelatin by the action of the calcium chloride and BMP is extracted from the gelatin in the form of a BMP urea solution. Extraction is complete after shaking at room temperature for approximately three days. The BMP-urea solution is thereafter filtered as before. The cold liquid fraction is dialyzed in dialysis bags against water containing 5 m.moles/l. sodium azide until the perfusate is free of urea and chloride ion, at which point a BMP precipitate forms in the cold water phase in the dialysis bag.

At this point in the process the BMP may be further purified by either of the two following procedures:

(a) The BMP precipitate is separated from the aqueous phase by centrifugation and then resolubilized by the addition of aqueous 6M urea. Thereafter the BMP from the BMP-urea solution as a coprecipitate with calcium phosphate. The calcium phosphate precipitate is formed by addition of calcium chloride and sodium phosphate to the BMP-urea solution. The coprecipitate is washed with cold deionized water and thereafter freeze dried for storage preparatory to use.

(b) Alternatively, the BMP precipitate subsequent to dialysis is treated with an aqueous solution of cold citric acid to remove additional acid soluble impurities from acid insoluble proteins including BMP. The precipitate is washed with cold deionized water and resolubilized with aqueous 6M urea. The BMP-urea solution is passed through a gel filtration column (molecular seive) wherein the molecular weight fraction of BMP between about 1,000 and 100,000 is recovered preparatory to use.

BMP is bioassayed by implantation of weighed samples in a muscle pouch or a diffusion chamber in an allogeneic recipient. If the sample of BMP to be tested is from another species, for example a test of human BMP in a laboratory animal, the recipient is an athymic mouse because it is immunodeficient and permits tests of biologically active proteins without the interference of an immune response. The more highly purified the sample of BMP, the better it is tolerated in a cross-species bioassay.

BMP has been further purified by Sepharose 6B chromatography. BMP has also been further purified by DEAE ion exchange chromatography and by isoelectric focusing.

EXAMPLE 2

An example of a practical application is implantation of BMP in a bone defect caused by injury, oil infection, malignancy, and congenital defects. In the form of a freeze dried coprecipitate with calcium phosphate, 1 mg. of BMP is implanted in a bone defect in which it stimulates differentiation of connective tissue into bone and thereby repairs the defect. Within about three weeks of implantation grossly visible evidence of new bone is noted. After about six months remodeling has been substantially complete and about 1 gram of bone is produced for each milligram of BMP implanted.

It will be understood that it is intended to cover all changes and modifications of the examples of the invention herein chosen for the purpose of illustration which do not constitute departures from the spirit and scope of the invention.

I claim:

1. Bone morphogenetic protein (BMP) made by the process comprising the steps of:
   (a) demineralizing bone tissue;
   (b) treating said demineralized bone tissue under aqueous conditions with a water soluble neutral salt and a solubilizing agent for said BMP, said agent being selected from the group consisting of urea and guanidine, and thereby transforming the bone collagen to gelatin and extracting BMP into said solution of solubilizing agent; and
   (c) separating said solubilizing agent and neutral salt from said solution, thereby precipitating BMP in the aqueous medium, and
said BMP has a molecular weight in the range of 1,000–100,000.

2. The BMP of claim 1, where in said separating step said solubilizing agent and neutral salt are separated from said solution by dialysis thereby precipitating BMP in the aqueous medium.

3. The BMP of claim 2, including the subsequent step of adding to said BMP precipitate, a solubilizing agent for said BMP precipitate selected from the group consisting of urea and guanidine thereby solubilizing said BMP.

4. The BMP of claim 3, including the step of washing said BMP precipitate from said dialysis step with citric acid prior to said addition of a solubilizing agent.

5. The BMP of claim 3, including the subsequent step of coprecipitating BMP and a calcium salt from said solution of BMP.

6. The BMP of claim 2, wherein said neutral salt is a physiologically acceptable salt.

7. The BMP of claim 2, wherein said solubilizing agent is urea, and said neutral salt is a chloride salt.

8. The BMP of claim 7, wherein said neutral salt is calcium chloride.

9. The BMP of claim 7, wherein said neutral salt is selected from the group consisting of calcium chloride, sodium chloride, potassium chloride, lithium chloride and strontium chloride.

10. The BMP of claim 3, wherein said subsequently added solubilizing agent is urea.

11. The BMP of claim 4, including the step of gel filtering said solubilized BMP.

12. The BMP of claim 11, including the step of recovering a BMP fraction having a molecular weight in the range of between about 1,000 and 100,000.

13. The BMP of claim 12, wherein said solubilizing agents are urea, and said neutral salt is a physiologically acceptable chloride salt.

14. The BMP of claim 5, wherein said calcium salt is calcium phosphate.

15. The BMP of claim 5, wherein each BMP precipitation step is carried out in a low temperature environment.

16. The BMP of claim 8, wherein said calcium chloride is in a molar solution of about 0.5M.

17. The BMP of claim 10, wherein said urea is in a molar solution of about 6M.

18. The BMP of claim 3, wherein said BMP has a molecular weight in the range of between about 20,000 and 63,000.

19. The BMP of claim 3, wherein said BMP has a molecular weight in the range of between about 10,000 and 63,000.

20. The BMP of claim 3, wherein said BMP has a molecular weight in the range of between about 20,000 and 50,000.

* * * * *